United States Patent
Oelmüller et al.

(10) Patent No.: US 6,861,213 B2
(45) Date of Patent: Mar. 1, 2005

(54) USE OF COMPOSITIONS CONSISTING OF CATIONIC COMPOUNDS AND PROTON DONORS FOR STABILIZING AND/OR ISOLATING NUCLEIC ACIDS IN OR FROM MICRO-ORGANISMS SUCH AS PROKARYOTS, FUNGI, PROTOZOA OR ALGAE

(75) Inventors: Uwe Oelmüller, Erkrath (DE); Tanja Wille, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 10/312,432

(22) PCT Filed: Jun. 26, 2001

(86) PCT No.: PCT/EP01/07281

§ 371 (c)(1),
(2), (4) Date: Mar. 5, 2003

(87) PCT Pub. No.: WO02/00600

PCT Pub. Date: Jan. 3, 2002

(65) Prior Publication Data

US 2003/0165943 A1 Sep. 4, 2003

(51) Int. Cl.[7] .............................. C12Q 1/70; C12Q 1/68; G01N 33/53
(52) U.S. Cl. ................ 435/5; 435/6; 435/7.1; 435/7.2
(58) Field of Search .......................... 435/5, 6, 7.1, 7.2

(56) References Cited

U.S. PATENT DOCUMENTS

| | | | |
|---|---|---|---|
| 4,900,677 A | * | 2/1990 | Hewitt ...................... 435/259 |
| 5,010,183 A | | 4/1991 | Macfarlane ................... 536/27 |
| 5,275,708 A | | 1/1994 | Akins et al. .................. 204/828 |
| 5,300,635 A | | 4/1994 | Macfarlane ................. 536/26.4 |
| 5,891,921 A | | 4/1999 | Walker ........................ 514/642 |

FOREIGN PATENT DOCUMENTS

| | | |
|---|---|---|
| EP | 0 606 712 | 7/1994 |
| GB | 1 289 426 | 9/1972 |

OTHER PUBLICATIONS

Rex, Chisolm. "*Molecular Biology*".online posting. Jan. 26, 1995. Feb. 2, 2001.

* cited by examiner

*Primary Examiner*—Jezia Riley
(74) *Attorney, Agent, or Firm*—Yankwich & Associates, P.C.; Leon R. Yankwich; Michael R. Wesolowski

(57) ABSTRACT

The present invention relates to the use of compositions for isolating and/or stabilizing nucleic acids in or from microorganisms—such as prokaryotes, fungi, protozoa or algae. The composition contains, as an essential ingredient, a cationic compound of general formula $$Y^+R_1R_2R_3R_4X^-$$

wherein

Y may denote nitrogen or phosphorus, $R_1$, $R_2$, $R_3$ and $R_4$ independently of one another may denote an unbranched or branched $C_1$–$C_{20}$-alkyl and/or a $C_6$–$C_{20}$-aryl group as well as a $C_6$–$C_{26}$-aralkyl group, and $X^-$ may denote an anion of an inorganic or organic, mono- or polybasic acid.

40 Claims, 6 Drawing Sheets

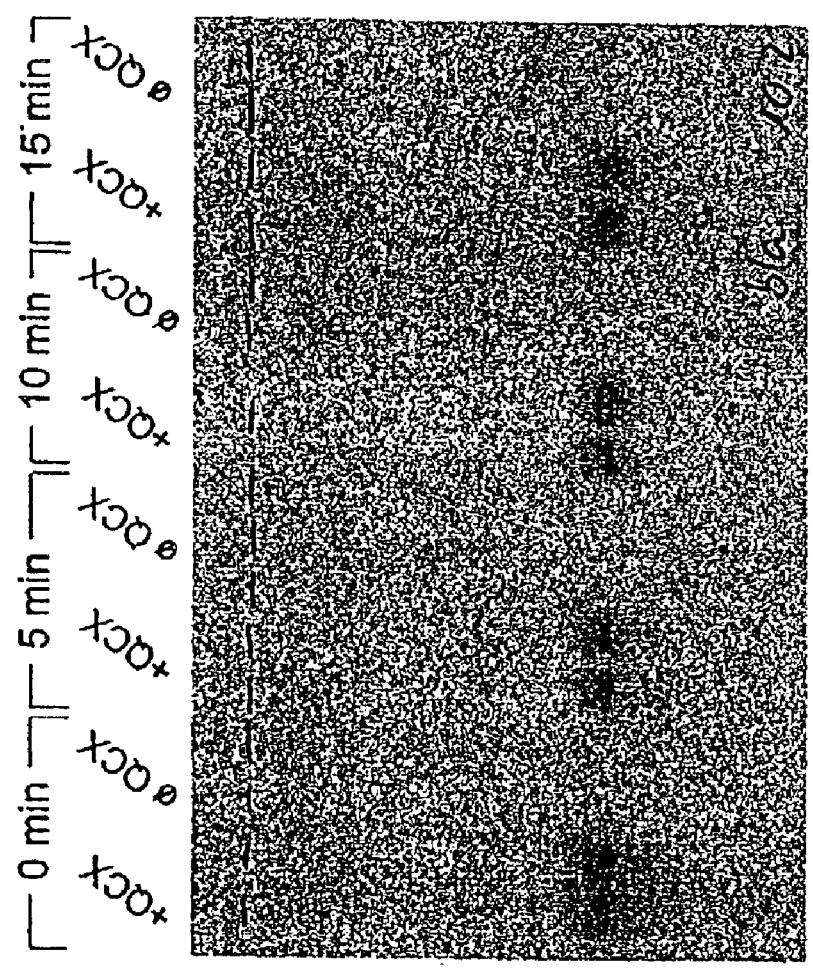

USE OF COMPOSITIONS CONSISTING OF CATIONIC COMPOUNDS AND PROTON DONORS FOR STABILIZING AND/OR ISOLATING NUCLEIC ACIDS IN OR FROM MICRO-ORGANISMS SUCH AS PROKARYOTS, FUNGI, PROTOZOA OR ALGAE

This application is a United States national filing under 35 U.S.C. §371 of international (PCT) application No. PCT/EP01/07281, filed Jun. 26, 2001, which claims priority to German Application No. 100 31 236.5, filed Jun. 27, 2000.

The present invention relates to a new use of compositions which [contain] as essential ingredient a cationic compound of general formula $$Y^+R_1R_2R_3R_4X^-$$

wherein

Y may denote nitrogen or phosphorus $R_1$, $R_2$, $R_3$ and $R_4$ independently of one another may denote an unbranched or branched $C_1$–$C_{20}$-alkyl and/or a $C_6$–$C_{20}$-aryl group as well as a $C_7$–$C_{26}$-aralkyl group and $X^-$ may denote an anion of an inorganic or organic, mono- or polybasic acid and at least one proton donor, as an additive for stabilising and/or isolating RNA and/or DNA from microorganisms—such as prokaryotes, fungi, protozoa or algae.

Preferred compositions are those wherein the cationic compounds consist of an ammonium salt wherein $R_1$ denotes a higher alkyl group—preferably with 12, 14 or 16 carbon atoms—and $R_2$, $R_3$ and $R_4$ in each case denote a methyl group.

Also preferred are compositions wherein $R_1$ denotes an aralkyl group—preferably a benzyl group, $R_2$ denotes a higher alkyl group—preferably with 12, 14 or 16 carbon atoms—and $R_3$ and $R_4$ denote a methyl group.

Preferred anions are bromide, chloride, phosphate, sulphate, formate, acetate, propionate, oxalate, malonate or succinate.

$C_1$–$C_6$-alkyl generally denotes a branched or unbranched hydrocarbon group with 1 to 6 carbon atom(s) which may optionally be substituted by one or more halogen atom(s)—preferably fluorine—which may be identical to or different from one another. The following hydrocarbon groups are mentioned by way of example:

methyl, ethyl, propyl, 1-methylethyl(iso-propyl), butyl, 1-methylpropyl, 2-methylpropyl, 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methyl-propyl.

The term higher alkyl group denotes a branched or unbranched $C_7$–$C_{20}$-alkyl group which may optionally be substituted by one or more halogen atom(s)—preferably fluorine—which may be identical to or different from one another. The following hydrocarbon groups are mentioned by way of example: branched or unbranched heptyl, octyl, nonyl, decyl, undecyl, dodecyl, tetradecyl, hexadecyl, dodecadecyl and eicosyl.

$C_3$–$C_6$-alkenyl generally denotes a branched or unbranched hydrocarbon group with 3 to 6 carbon atom(s), with one or possibly more double bonds, which may optionally be substituted by one or more halogen atom(s)—preferably fluorine—which may be identical to or different from one another. The following hydrocarbon groups are mentioned by way of example:

2-propenyl(allyl), 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 3-methyl-4-pentenyl, 4-methyl-4-pentenyl, 1,1-dimethyl-2-butenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl.

$C_3$–$C_6$-alkynyl generally denotes a branched or unbranched hydrocarbon group with 3 to 6 carbon atom(s), with one or possibly more triple bonds, which may optionally be substituted by one or more halogen atom(s)—preferably fluorine—which may be identical to or different from one another. The following hydrocarbon groups are mentioned by way of example:

2-propynyl(propargyl), 2-butynyl, 3-butynyl, 1-methyl-2-propynyl, 2-methyl-2-propynyl, 2-pentynyl, 3-pentynyl, 4-pentynyl, 1-methyl-2-butynyl, 2-methyl-2-butynyl, 3-methyl-2-butynyl, 1-methyl-3-butynyl, 2-methyl-3-butynyl, 3-methyl-3-butynyl, 1,1-dimethyl-2-propynyl, 1,2-dimethyl-2-propynyl, 1-ethyl-2-propynyl, 2-hexynyl, 3-hexynyl, 4-hexynyl, 5-hexynyl, 1-methyl-2-pentynyl, 2-methyl-2-pentynyl, 3-methyl-2-pentynyl, 4-methyl-2-pentynyl, 1-methyl-3-pentynyl, 2-methyl-3-pentynyl, 3-methyl-3-pentynyl, 4-methyl-3-pentynyl, 1-methyl-4-pentynyl, 3-methyl-4-pentynyl, 4-methyl-4-pentynyl, 1,1-dimethyl-2-butynyl, 1,1-dimethyl-2-butynyl, 1,1-dimethyl-3-butynyl, 1,2-dimethyl-2-butynyl, 1,2-dimethyl-3-butynyl, 1,3-dimethyl-2-butynyl, 1,3-dimethyl-3-butynyl, 2,2-dimethyl-2-butynyl, 2,3-dimethyl-3-butynyl, 1-ethyl-2-butynyl, 1-ethyl-3-butynyl, 2-ethyl-1-butynyl, 2-ethyl-2-butynyl, 2-ethyl-3-butynyl, 1,1,2-trimethyl-2-propynyl, 1-ethyl-1-methyl-2-propynyl and 1-ethyl-2-methyl-2-propynyl.

Unless otherwise defined, aryl denotes an aromatic mono- or polynuclear group with 4 to 22 C-atoms which may optionally contain one or two heteroatoms. Examples include: phenyl, naphthyl, anthracyl or pyrol, furan, thiophene, pyridine, pyridazine, pyrimidine or pyrazine, which may optionally be mono- or polysubstituted independently of one another by halogen (F, Cl, Br, I)—preferably fluorine—or by an alkyl group.

Aralkyl denotes a mono- or polynuclear aryl group in accordance with the above definition, which is bound to the cationic partial structure via a $C_1$–$C_6$-alkylene, $C_3$–$C_6$-alkenylene or $C_3$–$C_6$-alkynylene bridge, wherein the $C_1$–$C_6$-alkyl, $C_3$–$C_6$-alkenyl and $C_3$–$C_6$-alkynyl groups are as hereinbefore defined. For the purposes of the present invention the benzyl group is preferred.

Suitable counterions $X^-$ are preferably all the anions of hydrohalic acids or anions of mono- or dibasic organic acids such as the acetate or oxalate, malonate, succinate or citrate.

Suitable proton donors for the purposes of the present invention are, primarily, saturated aliphatic monocarboxylic acids, unsaturated alkenyl-carboxylic acids, saturated and/or unsaturated aliphatic $C_2$–$C_6$-dicarboxylic acids, aliphatic ketocarboxylic acids or ketodicarboxylic acids as well as amino acids, in addition to inorganic acids or the salts thereof, alone or in combination. All the abovementioned organic acids may be used in unsubstituted form or as substituted derivatives, of which—unless otherwise stated—the unsubstituted derivatives or derivatives mono- or polysubstituted by hydroxyl groups are preferred.

The term saturated aliphatic monocarboxylic acids for the purposes of the present invention preferably includes $C_1$–$C_6$-alkyl-carboxylic acids, in addition to formic acid, of which acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid and n-dodecanoic acid (lauric acid) are preferred. In addition, the ketocarboxylic acids derived from the abovementioned acids may also be used.

Examples of unsaturated alkenyl-carboxylic acids for the purposes of the present invention include acrylic acid (propenoic acid), methacrylic acid, crotonic acid, isocrotonic acid and vinylacetic acid.

According to the present invention saturated aliphatic $C_2$–$C_6$-dicarboxylic acids, such as for example oxalic acid, malonic acid, succinic acid, glutaric acid or adipic acid are preferred, while oxalic acid and succinic acid are particularly preferred.

It is particularly preferred, for solving the problem according to the invention, to use aliphatic hydroxy-di- and -tricarboxylic acids, of which tartronic acid, D-(+), L-(−)- or DL-malic acid, (2R, 3R)-(+)-tartaric acid, (2S, 3S)-(−)-tartaric acid, meso-tartaric acid and citric acid are most particularly preferred.

Thus, unsaturated dicarboxylic acids such as maleic or fumaric acid or unsaturated tricarboxylic acids, such as for example aconitic acid, are also suitable for solving the present problem.

For the purposes of the present invention, however, aliphatic ketodicarboxylic acids such as for example mesoxalic acid and oxaloacetic acid may also be used as additives, the oxaloacetic acid being most particularly preferred.

For the purposes of the present invention it is also possible to use amino acids, of which α-amino acids such as, e.g., aminoacetic acid (glycine), α-aminopropionic acid (alanine), α-amino-iso-valeric acid (valine), α-amino-iso-caproic acid (leucine) and α-amino-β-methylvaleric acid (isoleucine) are preferred. It is particularly preferable to use glycine.

The abovementioned proton donors may be used as individual substances or in the form of the pure stereoisomers and also in admixture.

Inorganic acids and the salts thereof may also be used as further additives for the purposes of the present invention. It is preferable to use the salts of inorganic acids—such as phosphoric acid or sulphuric acid—with alkali metals or the ammonium salts thereof. Most preferably, phosphoric acid and ammonium sulphate are used.

TABLE 1

| Name | Formula |
|---|---|
| acetic acid | $CH_3$—COOH |
| oxalic acid | HOOC—COOH |
| malonic acid | HOOC—$CH_2$—COOH |
| tartronic acid | HOOC—CHOH—COOH |
| succinic acid | HOOC—$CH_2$—$CH_2$—COOH |
| malic acid | HOOC—CHOH—$CH_2$—COOH |
| tartaric acid | HOOC—CHOH—CHOH—COOH |
| glutaric acid | HOOC—$CH_2$—$CH_2$—$CH_2$—COOH |
| adipic acid | HOOC—$CH_2$—$CH_2$—$CH_2$—$CH_2$—COOH |
| citric acid | HOOC—$CH_2$—COHCOOH—$CH_2$—COOH |
| maleic acid | HOOC—CH=CH—COOH |
| oxaloacetic acid | HOOC—CO—$CH_2$—COOH |
| glycine | $H_2N$—$CH_2$—COOH |

The additive may be present in the composition in various concentrations. It is also possible to use combinations of different additives. Depending on the nature of the additive, other concentration ranges may prove advantageous. It is also possible to use combinations of different additives.

The concentration of the cationic compound in the aqueous solution of the composition is in the range between 0.01% (w/v) and saturation, preferably between 0.1% and 10% (w/v) and saturation, more preferably between 0.5 and 8% (w/v) and most preferably between 2 and 6% (w/v).

Compositions of this kind are disclosed in the description of published German Application 100 31 236, the priority application on which the present application is based, as well as in claims 1 to 17.

Naturally, when adding a solution of cationic compounds and additive, the optimum concentrations are determined by the respective volume of the biological sample and the volume ratio by the volume of the stabilising solution and that of the biological sample.

Nucleic acids for the purposes of the invention—unless stated otherwise are nucleic acids in their wider sense, e.g. ribonucleic acids (RNA) which also comprise deoxyribonucleic acid in all lengths or configurations, such as double-stranded, single-stranded, circular and linear DNA and all possible subspecies such as, for example, monomeric nucleotides, oligomers, plasmids, bacterial DNA and RNA in processed and unprocessed form.

The biological sample used may be food samples or environmental samples which contain free or bound nucleic acids or microorganisms containing nucleic acids as envisaged according to the invention, such as for example organisms (single- or multi-cell organisms; insects, etc), plants and parts of plants, bacteria, viruses, yeasts and other fungi or prokaryotes.

The biological sample containing microorganisms for the purposes of the present invention, used as the starting material, may also be plasma, body fluids such as blood, serum, cells, leucocyte fractions, crusta phlogistica, sputum, urine, sperm, faeces, smears, aspirates, tissue samples of all kinds, such as biopsies, for example, parts of tissues and organs, food samples which contain free or bound nucleic acids or cells containing nucleic acid.

Apart from this, it is possible to stabilise nucleic acids originating from the abovementioned biological samples and of eukaryotic origin with the compositions according to the invention. Thus, it is possible to isolate or stabilise the materials of a eukaryotic nature mentioned in German Patent Application 100 31 236 (page 6, second paragraph of the documents as originally filed) according to the teaching of the present invention. In this way, according to the teaching of the present invention, nucleic acid of eukaryotic origin such as from blood, sputum or bone marrow can be successfully stabilised, as disclosed in Examples 1 to 15 and in FIGS. 1 to 15 of German Patent Application 100 31 236, to which reference is hereby made.

The additive may be present in the stabilisation reagent in various concentrations; for example it may be present in mixtures of the stabilising solution with blood in a ratio by volume of 1:1, preferably 3:1, in a concentration from 50 mM to saturation, preferably 100 to 1 M and most preferably in a concentration of 200–500 mM. Depending on the nature of the additive, other concentration ranges may prove advantageous. It is also possible to use combinations of different additives.

The concentration of the cationic compound in the aqueous solution of the composition is in the range between 0.01 wt. % and saturation, preferably between 0.1 wt. % and saturation, more preferably between 0.5 and 15 wt. % and most preferably between 2 and 10 wt. %.

Naturally, when adding a solution of cationic compounds and additive, the optimum concentrations are determined by the volume of the biological sample and the ratio by volume of the stabilising solution to the biological sample.

The pH of the mixture of cationic compound and additive—before mixing with the sample—may in general be varied as a function of the sample over a wide pH range (pH 2 to 12) and is preferably in a range from pH 2 to pH 10 and more preferably in a range from pH 3 to 8. The preferred pH range is dependent on the biological sample used. For blood, plasma and serum a pH value in a range between pH 2 and pH 6 and especially between pH 3 and pH 4 is preferred.

The pH of the mixture of cationic compound and additive may in general be varied as a function of the sample, the stabilisation and/or isolation of nucleic acids in or from microorganisms—such as prokaryotes, fungi, protozoa or algae—over a wide pH range (pH 2 to 12) and is preferably in a range from pH 2 to pH 8 and more preferably in a range from pH 2 to 5. The preferred pH range is dependent on the sample used.

For biological samples such as other cellular body fluids apart from blood, plasma and serum, or e.g. bacteria, aspirates, cells, tissues and other biological samples—such as those described above—the pH value in the stabilising solution consisting of cationic compound and additive is preferably in the range from pH 3 to pH 10 and more preferably in a range from pH 4 to pH 8. All the pH values given are to be understood as the pH before mixing with the biological sample.

To stabilise nucleic acids in biological samples, the sample may be mixed with a solution which contains the cationic compound(s) and additives. It is possible to add 0.1 to 10,000 volumes of the biological sample; preferably a volume ranging from 1 to 1000 is added, most preferably a volume in the range from 1 to 100. Depending on the nature of the sample, however, such as for example samples from fine needle biopsies or low cell count cultures, substantially higher volumes may also be used in some cases.

Similarly, the abovementioned cationic compounds and additives may also be added in solid form if the biological sample itself contains liquid to dissolve the solid (such as for example cell-containing body fluids, cells in medium, urine) or if liquid, e.g. water is added thereto to dissolve the solid. The advantage of adding a solid is that solids are usually chemically more stable and they are often easier to add to the sample.

Moreover, particularly with very compact biological samples such as tissues, for example, it is possible to grind up or homogenise the sample in the stabilising solution or before mixing it with the stabilising solution, in order to assist the release of nucleic acids or individual cells or cell aggregates, by destroying a compact sample by, for example, mechanical, chemical, physical or enzymatic action on the sample. Mechanical action may be carried out with an electric knife, a bead mill or by squeezing through a syringe, for example, while suitable enzymes for acting on the sample might be, for example, hydrolases, proteases or lipases.

In addition, the sample may be pre-treated by purely physical means, e.g. with ultrasound.

The pre-treatment may also be carried out chemically, either alone or in conjunction with purely physical methods. Means of assisting lysis include, for example, the use of aliphatic alcohols—particularly isopropanol—or aldehydes or dialdehydes—such as e.g. glyoxal—or also phenols or phenol derivatives—such as e.g. 2-biphenylol or ionic, zwitterionic and non-ionic compounds,—such as e.g. mercapto—or reducing reagents—such as e.g. dithiothreitol and β-mercaptoethanol—or phosphoric acid derivatives—such as e.g. tributylphosphate—or chaotropic reagents, such as e.g. urea, guanidinium thiocyanate or guanidinium hydrochloride—or salts, either individually or in combination.

Other possible ways of mechanically, chemically, physically or enzymatically acting on samples are known in the art and are intended to be included here.

The sample material may be stored for fairly long periods, depending on the particular requirements, such as e.g. from 1 to 14 days or longer, at ambient temperature, but also at elevated temperatures, such as e.g. 40° C. or more, and also at lower temperatures such as e.g. 4° C. or −20° C. or below.

The storage of the biological sample in the solution of the abovementioned compounds may either be followed directly by techniques for analysing nucleic acids, or the nucleic acids may be purified from the sample.

Regarding the technological background to the invention:

The investigation of RNA expression patterns in microorganisms by molecular-biological methods such as e.g. quantitative RT-PCR, NASBA, bDNA technology or biochips and Northern Blotting is used in basic research in the analysis of gene expression in prokaryotes, as well as in protozoa, fungi and algae and has also acquired increasing importance for example in medical diagnosis, in the identification of microbial pathogens, in the pharmaceutical industry for developing and evaluating pharmaceutical compositions, in biotechnology in the production of recombinant proteins for research and therapeutic applications, in ecology and population biology and also in food analysis for detecting contamination with microorganisms.

There is the problem that in order to isolate the nucleic acids the organisms have to be removed from their natural environment in order to obtain the cells for investigation and these then have to be transported to the place for isolation of the nucleic acid. At the same time there is a major risk that the RNA profiles and also the DNA will change. This would lead to wrong diagnosis or analysis of, for example, gene expressions in bacterial cultures or, for example, in medical/clinical diagnosis in an investigation of infected patient material (e.g. samples taken from sites of inflammation) forming the basis for the analysis of nucleic acids, or foods contaminated with bacteria, fungi, protozoa or algae. In food samples or clinical samples from patients the microorganisms may even die and the nucleic acids, particularly the RNA, are then broken down entirely. Therefore it is of maximum importance for the nucleic acids, particularly the RNA, to be stabilised immediately after the sample is taken.

A peculiarity of bacteria is the extremely rapid adaptation of their gene expression to the ambient conditions. The resulting short-lived changes in the gene expression pattern are possible because of very short half lives of the cellular mRNAs in bacteria and their ability to synthesise new RNA transcripts within a few seconds or minutes. These adaptation mechanisms are a problem in the analysis of prokaryotic RNA expression patterns as a change in the RNA expression pattern can take place even while the cells are being harvested and the procedure of RNA preparation is taking place. Thus, in subsequent analyses, it would no longer be the expression pattern under the defined experimental culture conditions that was considered but rather an RNA expression pattern which reflects the conditions during the harvesting, lysing or subsequent processing of the cell lysates.

Thus, the teaching of the present invention can also be applied to types of RNA other than mRNA, such as rRNA, snRNA, tRNA, Low Molecular Weight (LMW) RNA species but also to DNA such as genomic DNA (gDNA).

Conventional methods of isolating RNA from microorganisms such as prokaryotes, fungi, protozoa or algae, are based for example on the use of organic solvents such as phenol and chloroform (trichloromethane), on the use of chaotropic salts or combinations of these substances. In all the methods of isolating nucleic acids from prokaryotes, fungi, protozoa or algae known hitherto, the cells first have to be concentrated by centrifuging or filtration from the culture medium before further processing can take place. During this first step, in a very great number of cases, there is a change in the gene expression pattern in the cells on account of the changed ambient conditions (e.g. change in temperature, mechanical stress caused by centrifuging or filtration, change in gas atmosphere, etc), so that the gene expression pattern of the cells reflects not the culture conditions defined but the conditions of the process of isolation of the nucleic acids. Thus the validity of any subsequent analyses is called into question.

It is mainly the non-specific breakdown of RNA by RNases or by chemical influences such as deprotonation or the sequence-specific breakdown of RNA by RNases which break down special sequences, which is responsible for the change in the expression pattern. In addition, the new synthesis of RNA also has a disadvantageous and therefore undesirable influence.

Frequently, attempts are made to minimise this influence by very rapid cell harvesting and rapid cell decomposition but this cannot entirely prevent the change in the gene expression pattern. Moreover, it is impossible to process larger numbers of samples simultaneously. Moreover, enzymatic cell lysis was frequently avoided as it could only be done before the addition of organic solvents or concentrated chaotropic saline solutions and took at least three minutes. Thus, during enzymatic cell lysis it would be possible for enzymatic RNA degradation and new synthesis of RNA to take place at the same time, which would change the gene expression pattern of the cells. For this reason it was always disadvantageous, for subsequent gene expression analyses, to carry out enzymatic cell decomposition.

Another problem with the isolation of nucleic acids (RNA and DNA) from prokaryotes, fungi, algae and also protozoa is in the lysing of the cells as the cell wall has to be opened up for this. One method in widespread use is to digest the murein in the prokaryotic cell wall with the enzyme lysozyme; alternatively, other enzymes could also be used such as lysostaphin or proteinases. During the digestion the conditions in the sample being processed must be such as to guarantee the enzymatic activity of the corresponding enzyme. At the same time, however, such conditions usually also allow bacterial mRNA to be cleaved by RNases or allow the chemical hydrolysis of the nucleic acids, with the result that degraded nucleic acids are often obtained from the corresponding preparations. Furthermore, there is no guarantee that there will be no synthesis of nucleic acids during this enzymatic breakdown of the cells, which will additionally change the RNA expression pattern.

Regarding the object of the present invention:

The general object of the present invention is to avoid the disadvantages described above known from the prior art.

The object of the present invention is therefore to avoid processing-induced changes in the gene expression pattern during the isolation of nucleic acids from microorganisms such as bacteria, fungi (such as yeasts), protozoa or algae, so that the gene expression pattern of the cells reflects the specific culture conditions or the conditions in the original sample, such as a sample from a patient or a food sample, not the changes caused by the conditions of cell harvesting or the process of isolation of the nucleic acids, so as to ensure that any subsequent analyses are valid.

A further object of the present invention is to allow large numbers of samples to be processed in parallel at the same time in order to isolate RNA and DNA. The present invention also sets out to provide a composition in the form of a stabilising solution the ingredients of which are not damaging to health and which can therefore also be used, for example, to stabilise RNA and/or DNA in biological sample material during transportation from the place of removal to a laboratory without any health risks, such as occur when phenol is used, for example, to the staff dealing with the preparation of the samples.

The teaching of the present invention can be applied in particular to the Eubacteria, among the prokaryotes—in addition to the Archaebacteria (such as *Methanothermobacter marbirgensis*). The Eubacteria include Gram-positive as well as Gram-negative bacteria and also phototropic bacteria or *Chlamydia, Mycoplasma* (such as e.g. *Mycoplasma penetrans*), *Rickettsiae, Spirilla* and *Spirochetes* (such as *Borrelia burgdorferi*), to which the teaching of the invention can be applied.

Of the Gram-positive Eubacteria, *Bacillus* (such as e.g. *Bacillus subtilis*), *Staphylococcus* (such as for example *Staphylococcus aureus* or *Staphylococcus epidermis*), *Streptomyces* (such as for example *Streptomyces coelicotor* or *Streptomyces lividans*), *Flavobacterium* (such as for example *Flavobacterium johnsoniae*), *Mycobacterium* (such as for example *Mycobacterium avium*) or *Streptococcus* may be mentioned in particular.

The teaching of the present invention also applies to the following Gram-positive Eubacteria:
*Clostridiae* (such as e.g. *Clostridium difficile, Clostridium tetani* and *Clostridium perfringens*)
*Listeria*
*Peptococcus*
*Peptostreptococcus*
*Enterococcus*
*Corynebacterium* (such as e.g. *Corynebacterium diphtheriae* or *Corynebacterium glutamicum*)
*Propionibacterium*
*Lactobacillus*

The Gram-negative Eubacteria include in particular *Escherichia* (such as for example *Escherichia coli*), *Pseudomonas* (such as for example *Pseudomonas aeruginosa, Pseudomonas putida* or *Pseudomonas syringae*), *Klebsiella* (such as for example *Klebsiella*

*pneumoniae*), *Salmonella* (such as for example *Salmonella typhimurium*), *Sinorhizobium* (such as for example *Sinorhizobium meliloti*) or *Campylobacter*.

In addition, the teaching of the present invention also applies to the following Gram-negative bacteria:
*Neisseria* (such as e.g. *Neisseria gonorrhoae* or *Neisseria meningitidis*)
*Vibrio* (such as e.g. *Vibrio cholerae*)
*Shigella*
*Serratia*
*Enterobacter*
*Acinetobacter*
*Proteus*
*Yersinia*
*Brucella* (such as e.g. *Brucella abortus*)
*Haemophilus* (such as e.g. *Haemophilus influenza*)
*Bacteroides*
*Campylobacter*
*Helicobacter* (such as e.g. *Helicobacter pylori*)
*Bordetella*
*Legionella*
*Pasteurella*

Of the eukaryotes fungi deserve particular mention, including the fungi of the *Dermatophyte* group, the yeasts, moulds and biphasic fungi.

Of the yeasts special mention should be made of the genera *Saccharomyces* (such as for example *Saccharomyces cerevisiae*), *Candida* (such as e.g. *Candida albicans*), *Cryptococcus* (such as e.g. *Cryptococcus neoformans*). Of the moulds, special mention should be made of the genera *Aspergillus* (such as for example *Aspergillus fumigatus*) or *Penicillium* or *Mucor*.

Further examples of eukaryotes are the algae and protozoa—such as e.g. trypanosomes, toxoplasms, amoebae, plasmodia, Flagellata—to which the teaching of the invention may be applied.

Regarding the solution to the problem according to the invention:

The above-mentioned problems of the present invention are solved by bringing a defined culture of bacteria, fungus, protozoa or algae or a sample which contains bacteria and/or fungus and/or protozoa and/or algae into contact with the composition—or with the aqueous solution thereof—comprising a cationic compound of general formula 1 and at least one proton donor.

For subsequent harvesting of the cells and further working up of the sample, the cell wall, e.g. the murein basic structure of the bacterial cell wall, can be enzymatically digested with lysozyme, without the nucleic acids in the sample being subjected to any enzymatic or chemical degradation and with no new synthesis of nucleic acids, so as to prevent any changes to the RNA expression pattern.

Alternatively, other methods of enzymatic cell lysis are also possible, for example using lysostaphin, proteinase K, or a detergent-mediated cell lysis or combinations of these methods, i.e. with mechanical lysing methods.

Enzymatic cell lysis, unlike mechanical methods such as the use of a bead mill or grinding in liquid nitrogen, mainly has the advantage of being relatively easy to automate. Moreover, enzymatic cell lysis allows a high throughput of sample and minimises the risk of cross-contamination compared with the mechanical methods of cell lysis which are also known from the prior art.

In addition to the enzymatic cell lysis of bacteria there is also the option of lysing yeast cells using zymolase or lyticase, or a different lysing of eukaryotic cells with proteinase or other enzymes or using detergents after stabilising the cells with the compositions according to the invention.

Although enzymatic cell lysis is theoretically advantageous for the reasons stated, this process cannot really be used for analysing gene expression patterns as changes in the RNA expression pattern must be expected during this step when carrying out conventional methods of preparation. The use of the process described here provides one possible way of solving this problem, by stabilising the RNA in the cells even before the cells are harvested. In a subsequent step enzymatic cell lysis is possible, while enzymatic or chemical degradation of the RNA and new synthesis are prevented.

Instead of enzymatic cell lysis, mechanical, thermal or chemical cell lysis may be carried out, as well as combinations of one or more of the lysing methods mentioned above.

After the stabilisation and cell lysing the methods of isolating nucleic acids based on modified silica materials known from the prior art may be used for further processing of the sample.

The present invention provides a possible way of further processing the sample—for example in the isolation of RNA using organic solvents, chaotropic salts or by salting out the nucleic acids or by the use of magnetic particles or by hybrid capture methods.

Compared with the RNA extraction methods known hitherto from the prior art, such as TRIzol or RNeasy, by using the composition according to the invention comprising a cationic detergent of general formula I and a proton donor, in the form of an additive, preferably in the form of an aliphatic carboxylic acid, more preferably a dicarboxylic acid, of which tartaric acid is most particularly preferred, a yield is obtained which is 2 to 3 times greater than that obtained with the conventional methods mentioned above, for example.

This high RNA yield is particularly advantageous for the analysis of lowly expressed RNA transcripts or RNA transcripts which are expressed by only a subgroup of a bacterial population being analysed. Moreover, up till now there has been no workable method of isolating mRNA from bacteria, so that when analysing bacterial mRNAs the technician has to contend with a strong background of other RNA species (rRNA, tRNA, snRNPs). In such situations an increase in the sensitivity of the analytical processes must be assumed on account of the increased yield.

The advantages of the invention reside particularly in all the applications in which analyses of gene expression patterns in microorganisms (prokaryotes, protozoa, fungi, algae) have to be carried out. Such applications include for example scientific studies which contribute to a basic understanding of the regulation of prokaryotic gene expression, and also studies in which the correlation between the expression of selected genes and the pathogenicity of bacteria is analysed. This latter question is particularly relevant in diagnosis and for the treatment of bacterial infections.

Another important field of application of the invention is in the analysis of gene expression in prokaryotes, protozoa and fungi in pharmaceutical research and development. The stabilisation of e.g. prokaryotic RNA expression patterns considerably simplifies the analysis of transcript mirrors or complete expression patterns, possibly within the scope of experiments in which the time dependency of gene expression is to be demonstrated. In addition, the identification and quantifying of species in complex populations, for example bacteria in a soil sample or pathogens in samples from patients, is made much easier. Moreover, the potential applications also extend to other analytical areas such as food analysis, for example.

Stabilising nucleic acids using the composition of one or more cationic compound(s) and one or more additive(s)

according to the invention ensures that the nucleic acids in a sample do not change even when stored for lengthy periods or during transportation. Thus, the accuracy of tests carried out at a later stage is significantly increased. In certain cases, e.g. when the sample material has to be transported over long distances or stored for lengthy periods, the process according to the invention has made it possible for the first time for these tests to be carried out at all after such a period.

The advantages of this invention reside particularly both in the field of research, e.g. for analysing transcript levels which have to be fixed immediately after removal, and also in the field of clinical analyses, such as molecular diagnosis, for example, in which patient samples, once taken, have to be stabilised during storage and transportation until ready to be analysed.

In addition, the isolation and stabilisation of nucleic acids is used in tumour diagnosis, in the diagnosis of inherited diseases and in diagnosing and monitoring viruses and diagnosing and monitoring other infective agents, as well as in the analysis of gene expression patterns.

EXPLANATION OF THE FIGURES

FIG. 6 shows the bla (β-lactamase) Northern Blot analysis of *E. coli* RNA isolated after the addition of rifampicin with and without the use of the composition of cationic compound and additive or the aqueous solution thereof.

The following examples are intended to illustrate the present invention:

EXAMPLE 1
Isolation of RNA from *E. coli*

An aqueous solution consisting of 4% (w/v) tetradecylt- rimethylammonium oxalate and 200 mM of tartaric acid is adjusted to the following pH values with sodium hydroxide solution:

2.2 (without the addition of NaOH); 2.5; 3.0; 3.5; 4.0; 4.5 and 5.0.

25.

To perform the experiment, for each mixture, 2, 3 or 4 volumes of the detergent solution at the different pH values are pipetted into 400 μl aliquots of a culture of *E. coli* in LB medium, and the isolation of RNA is carried out by the following method:

addition of 400 μl of the *E. coli* culture to the prepared detergent solution, vortexing centrifuging 5000×g 10 min at 4° C.

decanting the supernatant resuspending the pellet in 1 ml H$_2$O centrifuging 5000×g 10 min at 4° C.

decanting the supernatant resuspending the pellet in 100 μl TE buffer[1] with 400 μg/ml lysozyme incubating for 5 min at ambient temperature addition of 300 μl RLT buffer[2], vortexing addition of 260 μl H$_2$O, vortexing addition of 40 μl Proteinase K (18 mg/ml), vortexing incubating for 10 min at 55° C.

centrifuging for 3 min, 14000×g removing the supernatant, adding 350 μl of 100% ethanol, vortexing charging the solution onto an RNeasy Mini spin column further processing as known from the prior art, e.g. as in the RNeasy® Mini procedure according to Messrs. QIAGEN, Hilden, for isolating total RNA from bacteria, Step 5 onwards.

[1] TE buffer consists of 10 mM Tris-HCl and 1 mM EDTA, which buffers at a pH of 8.
[2] RLT buffer denotes a standard commercial buffer (obtainable from Messrs. QIAGEN, Hilden) based on a guanidinium salt such as e.g. guanidinium isothiocyanate and an alkali metal salt of a polybasic organic acid as well as β-mercaptoethanol, which buffers at pH 7.

Figure 1:
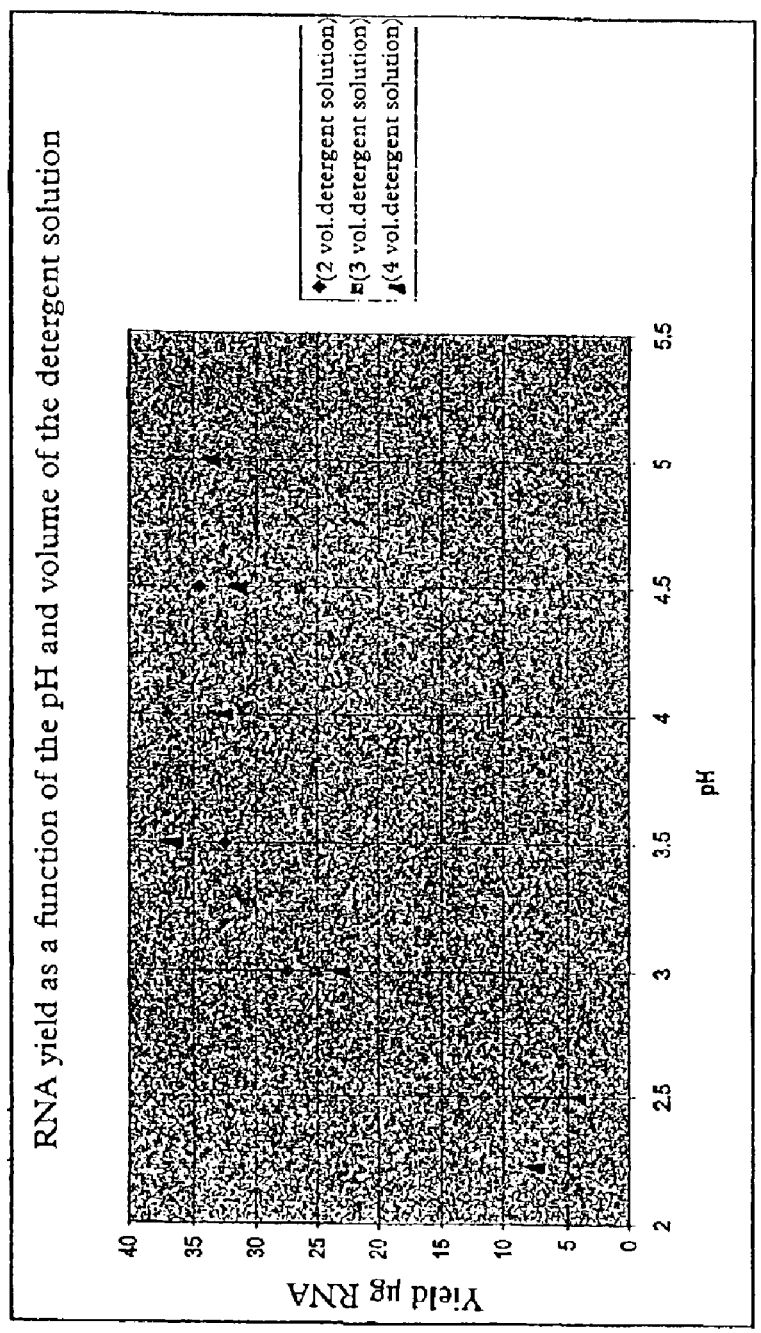
FIG. 1 graphically shows the dependency of the RNA yield on the pH of the detergent solution and the ratio by volume of culture to detergent solution.

FIG. 1 shows the RNA yield as a function of the pH of the detergent solution and the ratio by volume between culture and detergent solution.

The results obtained also show that the highest yields of RNA are obtained when the aqueous solution of the composition according to the invention has a pH in the range from 3.5 to 5.0.

The intactness of the RNA is analysed by agarose gel electrophoresis. In every case, intact ribosomal RNA bands are found.

EXAMPLE 2
Isolation of RNA from *E. coli* by Different Alternative Procedures The starting material for the experiments collected in this Example is again an *E. coli* culture grown in LB medium. All the different alternative procedures are carried out using 1.5×10$^8$ and 3×10$^8$ cells. For this series of experiments an aqueous solution of the composition according to the invention is used having the following composition:

4% (w/v) tetradecyl-trimethyl-ammonium oxalate 200 mM tartaric acid with a pH of 4.0

Starting from the following partial steps of the RNA isolation method, various alternative procedures are tried:

1) Cell Harvesting

Add 3 volumes of detergent solution to the *E. coli* culture, vortex, centrifuge, 5000×g 10 min at 4° C. decant the supernatant 2) Washing the Pellet Resuspend the pellet in 1 ml H$_2$O, centrifuge 5000×g 10 min at 4° C., decant the supernatant 3) Lysozyme Digestion Resuspend the pellet in 100 μl TE buffer with 400 μg/ml lysozyme, incubate for 5 min at ambient temperature 4) Establish the Binding Conditions Add 350 μl RLT buffer, vortex, add 250 μl of 100% ethanol 5) Proteinase K Digestion Add 300 μl RLT buffer, vortex, add 260 μl H2O, add 40 μl Proteinase K (18 mg/ml), vortex, incubate 10 min 55° C., centrifuge 3 min 14000×g, remove the supernatant, add 350 μl 100% ethanol, vortex 6) Lysozyme Digestion and Proteinase K Digestion in Dilute RLT Buffer Add 300 μl RLT buffer, vortex, add 160 μl H₂O, vortex, add 100 μl TE buffer with 400 μg/ml lysoz incubate for 5 min at ambient temperature, add 40 μl proteinase K (18 mg/ml), vortex, incubate for 10 min 55° C., centrifuge 3 min 14000×g, remove the supernatant, add 350 μl 100% ethanol, vortex 7) Working up using an optionally modified silica column—such as e.g. the RNeasy Mini spin column (obtainable from Messrs QIAGEN, Hilden)—Charge the solution onto the column, further processing acc. to RNeasy Mini method of isolating total RNA from bacteria, Step 5

The initial procedure is compared with the following alternative methods:
Variant 1: Steps 1); 3); 4) and 7)
Variant 2: Steps 1); 2); 3); 4) and 7)
Variant 3: Steps 1); 2), 3); 5) and 7) (initial procedure as in Example 1)
Variant 4: Steps 1); 6) and 7)

Figure 2:
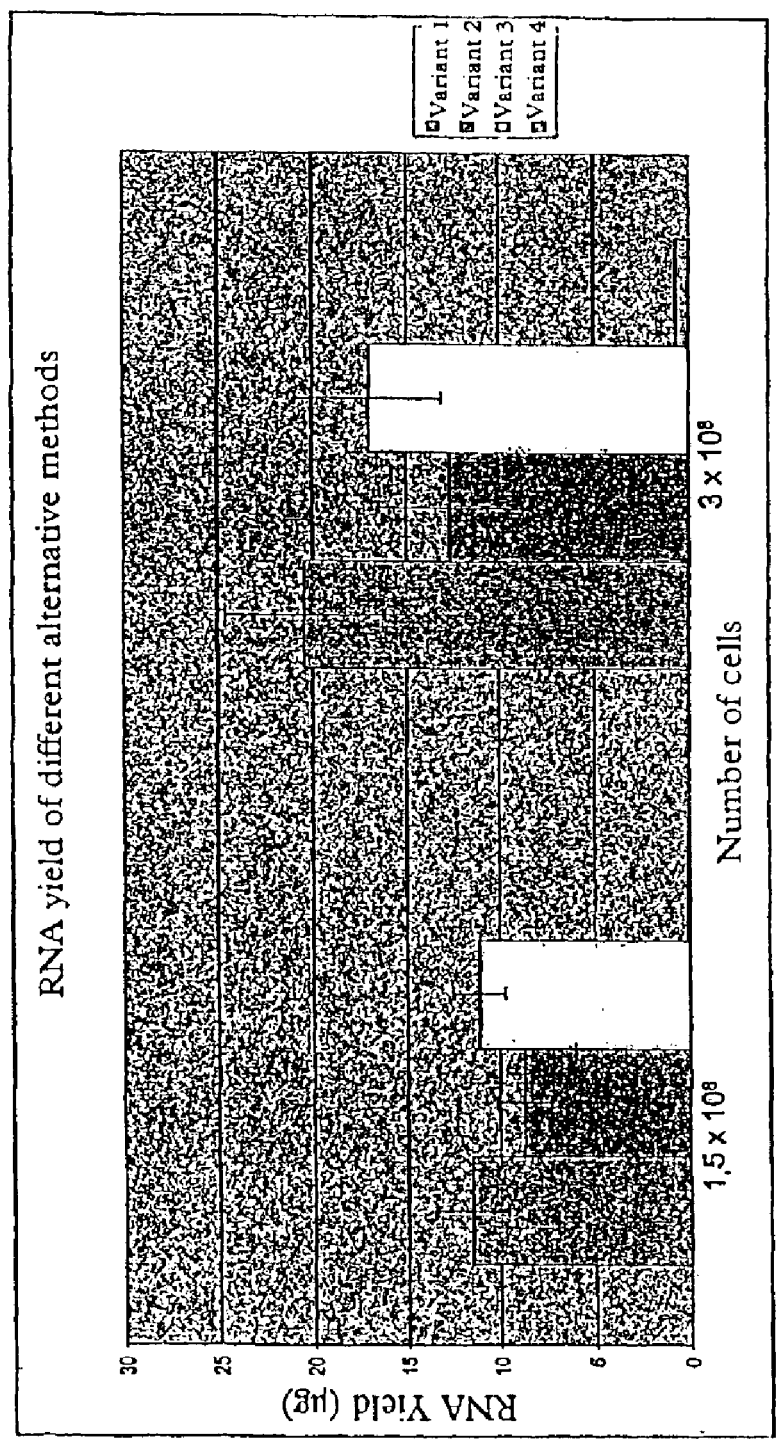
FIG. 2 graphically shows the dependency of the RNA yield on the different variants of the method.

FIG. 2 shows the RNA yield of the different alternative methods.

The results of these experiments provide a clear indication that carrying out variant 1 is comparable with the initial procedure (variant 3) in terms of the RNA yield. In this variant, there is no washing step or proteinase K digestion. Thus, the working up process as a whole is substantially shortened, and consequently this variant is used as the standard method in the Examples that follow.

EXAMPLE 3

Isolation of RNA from *E. coli* with different ratios by volume of culture to aqueous solution of the composition according to the invention.

Aqueous solutions of the composition according to the invention are used having the following composition:

| | |
|---|---|
| solution QCX 1 | 4% (w/v) tetradecyl trimethylammonium oxalate<br>200 mM tartaric acid<br>pH 4.0 |
| solution QCX 2 | 6% (w/v) tetradecyl trimethylammonium oxalate<br>300 mM tartaric acid<br>pH 4.0 |
| solution QCX 3 | 8% (w/v) tetradecyl trimethylammonium oxalate<br>400 mM tartaric acid<br>pH 4.0 |
| solution QCX 4 | 15% (w/v) tetradecyl trimethylammonium oxalate<br>750 mM tartaric acid<br>pH 4.0 |

400 μl aliquots of an *E. coli* culture grown in LB medium (10 g Trypton; 5 g yeast extract; 10 g NaCl; H₂O ad 1000 ml) are combined with 2, 3 or 4 volumes of the appropriate solutions and worked up by the standard method defined in Example 2.

Figure 3:
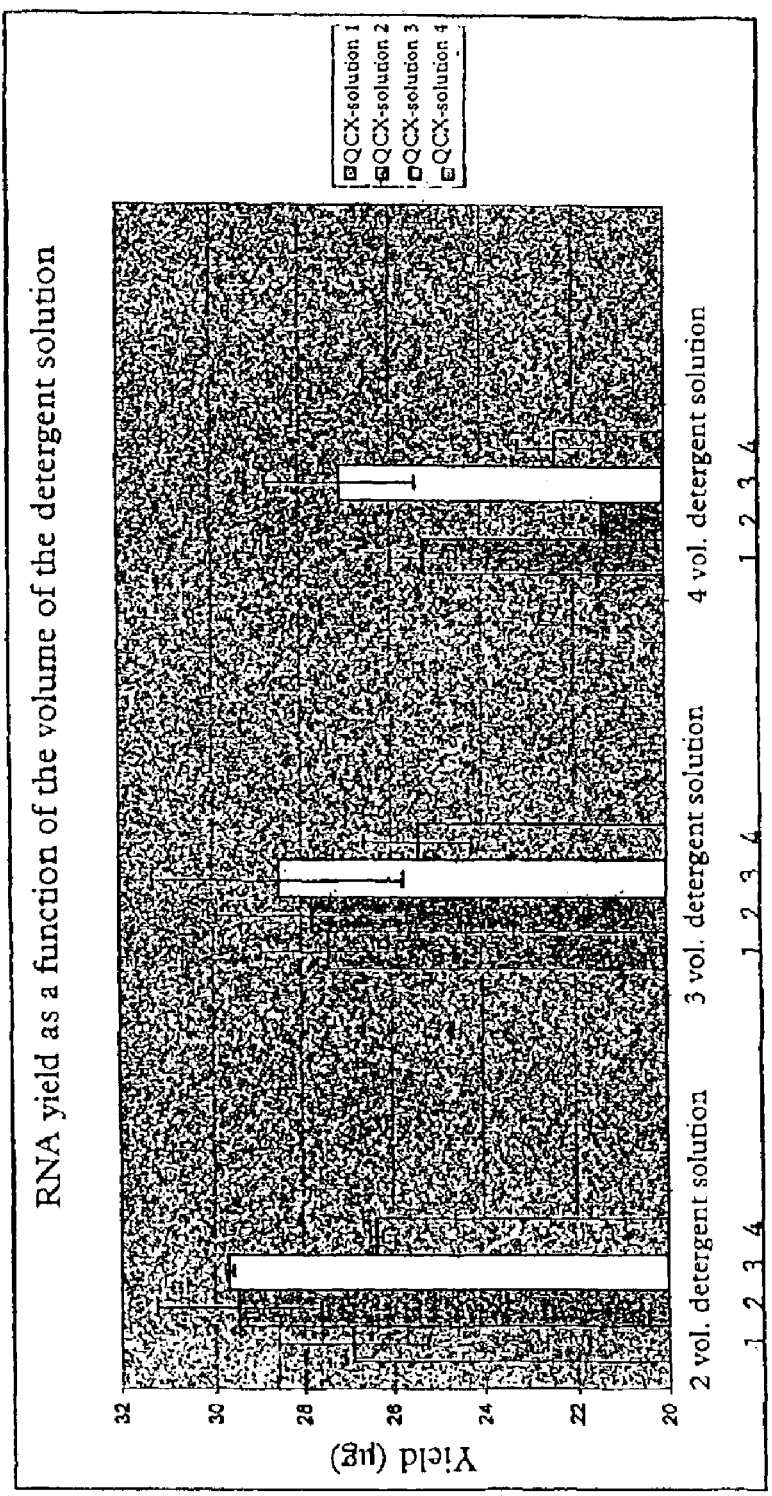
FIG. 3 graphically shows the RNA yield as a function of the volume of the aqueous solution of the compound according to the invention.

FIG. 3 shows the RNA yield as a function of the volume of the aqueous solution of the cationic compound according to formula 1 and additive.

As can be seen from the experimental findings, the RNA yields are thoroughly comparable when using 2 or 3 volumes of the various detergent solutions. When 4 volumes of the solutions described above are used there is a certain loss of RNA yield. In the mixtures using 2 or 3 volumes of the detergent solutions, yields are obtained which are comparable with those of solutions 1, 2 and 3.

Figure 4:
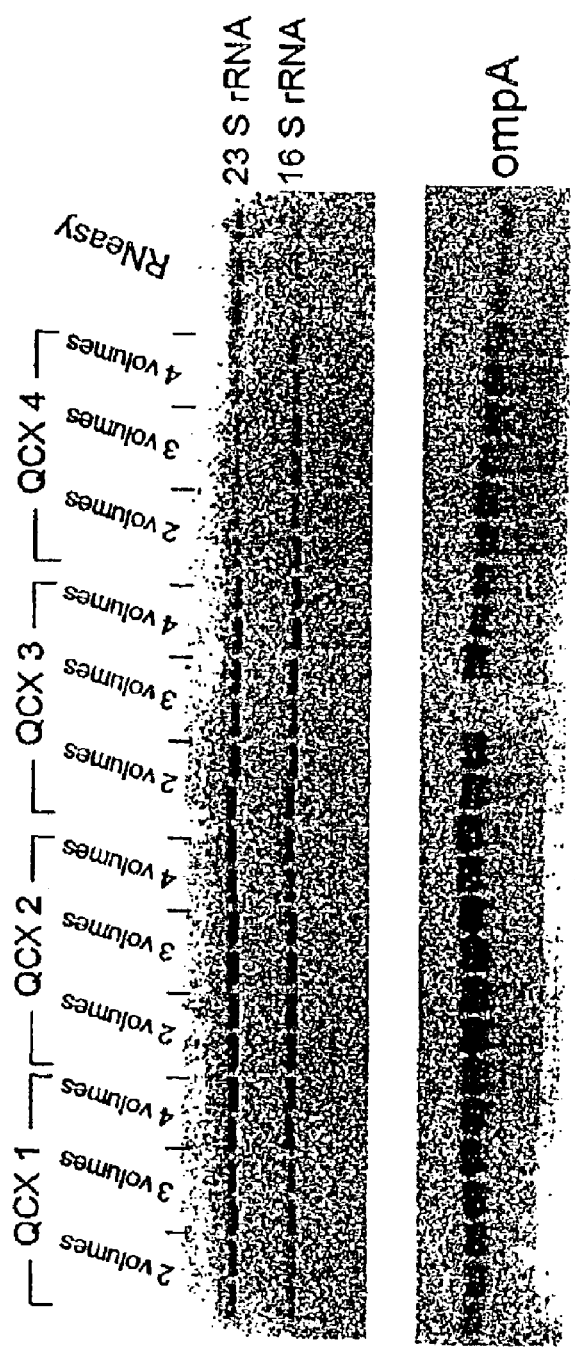
FIG. 4 shows the results of the denaturing agarose gel electrophoresis and ompA Northern Blot analysis of *E. coli* RNA isolated with solutions of different volumes of solutions of the composition of cationic compound and proton donor in various concentrations.

In order to assess the intactness of the isolated RNA, the RNA is separated on denaturing agarose gels and then a Northern Blot analysis is carried out (cf. FIG. 4!).

Visual analysis of the rRNA bands shows largely intact ribosomal RNA bands on the agarose gel. Only the bands obtained using solution 4 indicate a partial degradation of the RNA. This finding is confirmed by a Northern Blot analysis in which hybridisation is carried out with a probe directed against ompA ("outer membrane protein A"*) mRNA from *E. coli*.

*The ompA mRNA is a relatively long-lived RNA transcript with a half-life of 15 minutes (Nature 1984, 312: 75–77).

Once again, there is some degradation of the RNA isolated using solution 4. When the other RNA samples are compared the sharpest ompA mRNA bands are found in the traces in which RNA is isolated with solution 1. Overall, however, the RNA samples isolated with solutions 1–3 show only very slight differences in the quality of the RNA.

FIG. 4 shows the results of the denaturing agarose gel electrophoresis and ompA Northern Blot analysis of *E. coli* RNA isolated with solutions of different volumes and concentrations.

EXAMPLE 4

Stabilising *E. coli* RNA.

In order to assess the stabilising efficiency, in this Example experiments are carried out in which the RNA polymerase inhibitor rifampicin is added to the *E. coli* cells in the culture medium (FEBS Letters 1998, 440: 172–174). This prevents the new synthesis of RNA transcripts, thus making analysis of the degradation of RNA transcripts easier. At specified times after the addition of the inhibitor the RNA is isolated from the cells. The controls used are mixtures which are subjected to analogous processes but wherein the RNA is isolated without adding the solution (RNeasy standard method). To assess the intactness of the mRNA, Northern Blot experiments are carried out after the isolation of the RNA.

Figure 5:
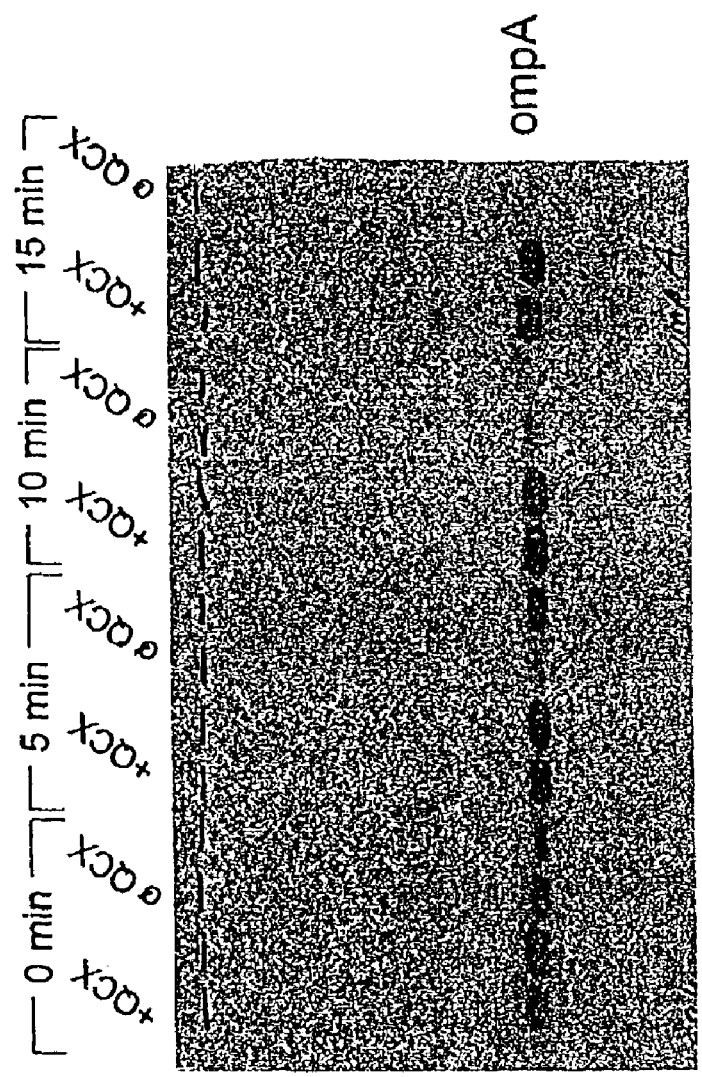
FIG. 5 shows the ompA ("outer membrane protein A") Northern Blot analysis of *E. coli* RNA isolated after the addition of rifampicin with and without dissolution of the composition according to the invention.

FIG. 5 shows the ompA ("outer membrane protein A") Northern Blot analysis of *E. coli* RNA isolated after the addition of rifampicin with or without dissolving the composition according to the invention.

The ompA mRNA is an *E. coli* transcript which has a half-life of 15 minutes under the culture conditions used (Nature, 1984, 312: 75–77). The Northern Blot analysis (FIG. 5) shows that in the samples which are treated with the solution according to the invention, a signal of uniform intensity for the ompA mRNA can be detected over the entire period of investigation (up to 15 minutes). By contrast, for the ompA mRNA in the samples without the added detergent, a significant loss of the transcript is observed after only 0 to 5 minutes.

FIG. 6 shows bla (β-lactamase) Northern Blot analysis of *E. coli* RNA isolated after the addition of rifampicin with or without using the composition or the aqueous solution of cationic compound and additive.

In Northern Blot analysis the same effect is even more clearly detectable for the β-lactamase mRNA (bla). This mRNA transcript has a half-life of 2–5 minutes under the culture conditions chosen (Nature, 1984, 312: 75–77). As is apparent from FIG. 6, this transcript can be detected in the RNA samples isolated with the addition of the solution with a comparable signal intensity over the entire period of investigation. In the control batches without the detergent solution, on the other hand, there is an almost total loss of the bla mRNA transcript even if the RNA is worked up immediately (0 minutes). The difference in bla mRNA signal intensities between the two methods of isolating RNA reflects the immediate stabilisation of the mRNA by the corresponding aqueous solution of the composition according to the invention.

These experiments show that the composition according to the invention opens up the possibility of fixing RNA expression profiles of bacteria in the state of liquid culture without any artefacts from the isolation process leading to a distortion of the expression pattern.

EXAMPLE 5

RNA Stabilisation with Tetradecyl Trimethylammonium Bromide (TTAB).

In the following experiments a TTAB solution with the following composition is used:

4% (w/v) TTAB
200 mM tartaric acid
pH 4.0

Different species of bacteria differ in the nature of their cell wall, inter alia. When different species are used, the cell lysis is a critical step in the isolation of the RNA. Compared with enzymatic cell lysis, which gives good results particularly for Gram-negative species of bacteria, mechanical cell lysis potentially has the ability to lyse all kinds of species.

The following Table shows a comparison of the different yields which are obtained on the one hand using methods according to the prior art (RNeasy with lysozyme-mediated cell lysis), using the composition according to the invention and RNeasy including lysozyme digestion, and also using the composition according to the invention and RNeasy, the enzymatic cell lysis being assisted by the use of a bead mill. When the bead mill was used (MM 300 of Messrs QIAGEN) 50 mg of acid-washed glass beads (diameter 150–600 µm) were used per batch. The cell lysing in the bead mill was carried out for 5 min at maximum vibration speed (30 Hz).

TABLE 2

RNA yields from $1 \times 10^8$ cells of *B. subtilis* with different methods of cell lysis followed by RNA isolation with RNeasy ®

| cell lysis | lysozyme digestion | TTAB solution + lysozyme digestion | TTAB solution + bead mill + lysozyme digestion |
|---|---|---|---|
| *B. subtilis* in LB medium | 7 µg | 15 µg | 19 µg |
| *B. subtilis* in mineral medium | 3 µg | 8 µg | 10 µg |

As is clear from the comparison, the RNA isolation with the solution of the composition according to the invention, in conjunction with mechanical cell lysis, leads to roughly a 25% rise in the increase, compared with enzymatic cell lysis using the solution (Table 2). Compared with RNA isolation according to the RNeasy standard method, on average the yield was tripled by mechanical cell lysis using the detergent solution.

These results are a clear indication that enzymatic cell lysis using the detergent solution also proceeds efficiently in the Gram-positive *B. subtilis* cells, which means that mechanical cell lysis may optionally be omitted here.

However, the use of a mechanical method of lysing, such as the bead mill, with no enzymatic cell lysis, also opens up the possibility of achieving a roughly 6-fold increase in yield, compared with RNA isolation without enzymatic or mechanical cell lysis, as is clearly demonstrated by the following experimental findings:

The starting material used is a culture of *Bacillus subtilis* grown in LB medium. The RNA yields from $1.8 \times 10^8$ cells per mixture, in each case, are compared (Table 3). In some of the samples the cell lysis is carried out with a bead mill (MM300 made by Messrs QIAGEN) using 50 mg of acid-washed glass beads (diameter 150–600 µm) per batch. The cell lysis in the bead mill was carried out for 5 minutes at maximum vibrating speed (30 Hz). In another group of samples there was neither enzymatic nor mechanical lysing of the cells (reference: J. Microbiol. Methods 44 (2001): 235–238) Promega "SV Total RNA Isolation System".

TABLE 3

RNA yield from *Bacillus subtilis* as a function of the cell lysis method and the addition of the TTAB solution

| | without enzymatic or mechanical cell lysis | mechanical cell lysis |
|---|---|---|
| use of the TTAB solution | 3 µg | 18 µg |

What is claimed is:

1. A method for stabilizing nucleic acids in or from microorganisms comprising administering to the microorganism a composition containing a cationic compound of general formula 1:

$$Y^+R_1R_2R_3R_4X^- \qquad (1)$$

wherein

Y represents nitrogen or phosphorus;

$R_1$, $R_2$, $R_3$ and $R_4$, independently, represent an unbranched or branched $C_1$–$C_{20}$-alkyl group and/or a $C_7$–$C_{20}$-aryl group as well as a $C_6$–$C_{26}$-arallcyl group;

$X^-$ represents an anion of an inorganic or organic, mono- or polybasic acid; and at least one proton donor.

2. The method according to claim 1, wherein Y denotes nitrogen.

3. The method according to claim 1, wherein $R_1$ denotes a higher alkyl group with 12, 14 or 16 carbon atoms and $R_2$, $R_3$ and $R_4$ each represent a methyl group.

4. The method according to claim 1 or 3, wherein the anion $X^-$ is an anion of hydrohalic acids or anions of mono- or dibasic organic acids.

5. The method according to claim 4, wherein the anion is selected from the group consisting of bromide, chloride, phosphate, sulphate, formate, acetate, propionate, oxalate, malonate, succinate and citrate.

6. The method according claim 1, wherein the proton donor is selected from the group consisting of saturated aliphatic monocarboxylic acids, the unsaturated alkenyl-carboxylic acids, the saturated and/or unsaturated aliphatic $C_2$–$C_6$-dicarboxylic acids and/or tricarboxylic acids, the aliphatic ketodicarboxylic acids, the amino acids or the inorganic acids or the salts thereof, and combinations thereof.

7. The method according to claim 6, wherein the aliphatic monocarboxylic acid comprises a $C_1$–$C_6$-alkyl-carboxylic acid selected from the group consisting of acetic acid, propionic acid, n-butyric acid, n-valeric acid, isovaleric acid, ethyl-methyl-acetic acid (2-methyl-butyric acid), 2,2-dimethylpropionic acid (pivalic acid), n-hexanoic acid, n-octanoic acid, n-decanoic acid or n-dodecanoic acid (lauric acid) or mixtures thereof.

8. The method according to claim 6, wherein the aliphatic alkenyl-carboxylic acid is selected from the group consisting of acrylic acid (propenoic acid), methacrylic acid, crotonic acid, isocrotonic acid or vinylacetic acid or mixtures thereof.

9. The method according to claim 6, wherein the saturated aliphatic $C_2$–$C_6$-dicarboxylic acid is selected from the group consisting of oxalic acid, malonic acid, succinic acid, glutaric acid or adipic acid or mixtures thereof.

10. The method according to claim 9, wherein the aliphatic dicarboxylic acid is oxalic acid or succinic acid or mixtures thereof.

11. The method according to claim 6, wherein the aliphatic hydroxy-di- and -tricarboxylic acids are selected from the group consisting of tartronic acid, D-(+), L-(−)- or DL-malic acid, (2R,3R)-(+)-tartaric acid, (2S,3S)-(−)-tartaric acid, meso-tartaric acid, citric acid, and mixtures thereof.

12. The method according to claim 6, wherein the unsaturated dicarboxylic acid is maleic and/or fumaric acid or mixtures thereof.

13. The method according to claim 6, wherein the unsaturated tricarboxylic acid is aconitic acid.

14. The method according to claim 6, wherein the aliphatic ketodicarboxylic acids are mesoxalic acid or oxaloacetic acid, or mixtures thereof.

15. The method according to claim 6, wherein the amino acids are selected from the group consisting of aminoacetic acid (glycine), α-aminopropionic acid (alanine), α-amino-iso-valeric acid (valine), α-amino-iso-caproic acid (leucine) and α-amino-β-methylvaleric acid (isoleucine), and mixtures thereof.

16. The method according to claim 1, wherein the composition is in the form of an aqueous solution.

17. The method according to claim 16, wherein the cationic compound is present in the composition in a concentration in a range from 0.01% (W/V) to 10% (W/V).

18. The method according to claim 1, wherein the nucleic acids originate from prokaryotes, the Archaebacteria or the Eubacteria.

19. The method according to claim 18, wherein the nucleic acids originate from Gram-positive bacteria.

20. The method according to claim 19, wherein the nucleic acids originate from *Bacillus, Staphylococcus, Streptomyces, Flavobacterium, Mycobacterium, Streptococcus, Clostridiae, Listeria, Peptococcus, Peptostreptococcus, Enterococcus, Corynebacterium, Propionibacterium* or *Lactobacillus*.

21. The method according to claim 18, wherein the nucleic acids originate from Gram-negative bacteria.

22. The method according to claim 21, wherein the nucleic acids originate from *Escherichia, Pseudomonas, Klebsiella, Salmonella, Sinorhizobium, Campylobacter, Neisseria, Vibrio, Shigella, Serratia, Enterobacter, Acinetobacter, Proteus, Yersinia, Brucella, Haemophilus, Bacteroides, Helicobacter, Bordetella, Legionella* or *Pasteurella*.

23. The method according to claim 18, wherein the nucleic acids originate from *Chlamydia*.

24. The method according to claim 18, wherein the nucleic acids originate from phototropic bacteria.

25. The method according to claim 18, wherein the nucleic acids originate from *Mycoplasma*.

26. The method according to claim 18, wherein the nucleic acids originate from *Rickettsia*.

27. The method according to claim 18, wherein the nucleic acids originate from *Spirochetes*.

28. The method according to claim 18, wherein the nucleic acids originate from *Spirilla*.

29. The method according to claim 1, wherein the nucleic acids originate from eukaryotic microorganisms.

30. The method according to claim 29, wherein the nucleic acids originate from fungi of the Dermatophyte group, the yeasts, the moulds and the biphasic fungi.

31. The method according to claim 30, wherein the nucleic acids originate from the yeasts *Saccharomyces, Candida* or *Cryptococcus*.

32. The method according to claim 30, wherein the nucleic acids originate from moulds of the group *Aspergillus*.

33. The method according to claim 30, wherein the nucleic acids originate from moulds of the group *Penicillium*.

34. The method according to claim 30, wherein the nucleic acids originate from moulds of the group *Mucor*.

35. The method according to claim 29, wherein the nucleic acids originate from algae.

36. The method according to claim 29, wherein the nucleic acids originate from protozoa.

37. The method according to claim 1, wherein said microorganism is lysed by enzymatic, mechanical, thermal or chemical methods, or combination thereof.

38. The method according to claim 1, wherein said composition has a pH in the range from 2 to 12.

39. A kit for stabilization of nucleic acids in or from microorganisms comprising a composition according to claim 1 and instructions for combining said composition with a solution containing nucleic acids, in or from microorganisms, to be stabilized.

40. A mixture comprising a biological sample comprising prokaryotes, fungi, protozoa or algae and a composition according to claim 1, optionally together with other excipients.

* * * * *

UNITED STATES PATENT AND TRADEMARK OFFICE
CERTIFICATE OF CORRECTION

PATENT NO. : 6,861,213 B2
DATED : March 1, 2005
INVENTOR(S) : Oelmüller, Uwe et al.

It is certified that error appears in the above-identified patent and that said Letters Patent is hereby corrected as shown below:

Column 16,
Line 25, please delete "$C_7$- $C_{20}$ -aryl group" as well as a "$C_6$-$C_{26}$-arallcyl group" and insert therefor:
-- $C_7$-$C_{20}$-aryl group -- as well as a -- $C_6$-$C_{26}$-aralkyl group --

Signed and Sealed this

Nineteenth Day of July, 2005

JON W. DUDAS
*Director of the United States Patent and Trademark Office*